US007683611B2

(12) United States Patent
Burkhardt et al.

(10) Patent No.: US 7,683,611 B2
(45) Date of Patent: Mar. 23, 2010

(54) PIPELINE INSPECTION USING VARIABLE-DIAMETER REMOTE-FIELD EDDY CURRENT TECHNOLOGY

(75) Inventors: Gary Lane Burkhardt, Adkins, TX (US); Alfred Eugene Crouch, San Antonio, TX (US); Albert Joseph Parvin, Jr., San Antonio, TX (US); Ronald Herbert Peterson, Helotes, TX (US); Todd Hegert Goyen, San Antonio, TX (US); Richard Franklin Tennis, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 304 days.

(21) Appl. No.: 11/767,267

(22) Filed: Jun. 22, 2007

(65) Prior Publication Data

US 2008/0042646 A1    Feb. 21, 2008

Related U.S. Application Data

(60) Provisional application No. 60/805,697, filed on Jun. 23, 2006, provisional application No. 60/805,669, filed on Jun. 23, 2006.

(51) Int. Cl.
*G01N 27/82* (2006.01)
(52) U.S. Cl. ........................... 324/220; 324/240
(58) Field of Classification Search ......... 324/219–221, 324/228–229, 234, 236–243, 256–257
See application file for complete search history.

(56) References Cited

U.S. PATENT DOCUMENTS 3,529,236 A * 9/1970 Proctor .................. 324/220
4,769,598 A   9/1988 Krieg et al.
5,623,203 A   4/1997 Hosohara et al.
6,087,830 A   7/2000 Brandly et al.
6,127,823 A  10/2000 Atherton
6,917,176 B2  7/2005 Schempf
7,002,340 B2  2/2006 Atherton (Continued)

OTHER PUBLICATIONS

Fisher, J.L., "Remote-Field Eddy Current Inspection," ASM Handbook, p. 196-201, vol. 17, ASM Handbook Committee, Southwest Research Institute Library, San Antonio, TX.

(Continued)

*Primary Examiner*—Bot L LeDynh
(74) *Attorney, Agent, or Firm*—Grossman, Tucker et al.

(57) ABSTRACT

The present disclosure relates to a device and method for pipeline inspection. The inspection device may include an exciter coil capable of providing an alternating current magnetic field and producing eddy currents. A plurality of sensors may then be provided which are capable of sensing a magnetic field produced by the eddy currents and the sensors may be engaged with a sensor shoe. The sensors may then be capable of being positioned at a first distance $D_1$ with respect to an inner pipe wall surface and capable of providing coupling to the magnetic field produced by the eddy currents. The sensor shoe may also be capable of retracting to a second distance $D_2$, wherein $D_1 < D_2$. The sensor shoe may be connected to a sensor support arm wherein the support arm may be pivotably attached to a fixed hub and to a control arm which control arm may then be pivotably attached to a driven hub.

15 Claims, 14 Drawing Sheets

U.S. PATENT DOCUMENTS

| | | |
|---|---|---|
| 7,143,659 B2 | 12/2006 | Stout et al. |
| 7,154,264 B2 | 12/2006 | Burkhardt |
| 7,459,999 B2 | 12/2008 | Burkhardt |
| 2004/0189289 A1 | 9/2004 | Atherton |
| 2004/0217759 A1 | 11/2004 | Burkhardt et al. |

OTHER PUBLICATIONS

Sun, Yushi, et al., "Efforts Towards Gaining a Better Understanding of the Remote Field Eddy Current Phenomenon and Expanding its Applications,"IEEE Transactions on Magnetics, p. 1589-1592, May 1996, vol. 32, No. 3.

Tomita, K., et al., "Development of Remote Field Eddy Current Inspection System for Gas Distribution Pipes," Proceedings of the 1986 International Gas Research Conference: Toronto, Canada, Sep. 8-11, 1986, p. 126-134, Government Institutes.

Atherton, D., et al., "Investigations of the Remote Field Eddy Current Technique in Large Diameter Pipeline," British Journal of Non-Destructive Testing, p. 485-488, 1989, vol. 31, No. 9.

Schmidt, T.R., "The Remote Field Eddy Current Inspection Technique," Materials Evaluation, p. 225-230, Feb. 1984, vol. 42, No. 2.

Teitsma, A., et al., "Small diameter remote field eddy current inspection for unpiggable pipelines," Journal of Pressure Vessel Technology, pp. 269-273, Aug. 2005, vol. 127.

Teitsma, A., "Reduced Mandated Inspection by Remote Field Eddy Current Inspection of Unpiggable Pipelines," Technical Final Report, DE-FC26-04NT42266, Gas Technology Institute, Oct. 2006.

Teitsma, A., "Delivery Reliability for Natural Gas—Inspection Technologies," Technical Semiannual Progress Report, DE-FC26-04NT42266, Gas Technology Institute, Mar. 2004.

Teitsma, A., "Remote Field Eddy Current Inspection of Unpiggable Pipelines," Final Report, DE-FC26-02NT41647, Gas Technology Institute, Mar. 2004.

* cited by examiner

PIPELINE INSPECTION USING VARIABLE-DIAMETER REMOTE-FIELD EDDY CURRENT TECHNOLOGY

CROSS-REFERENCE TO RELATED APPLICATIONS

This application claims the benefit of U.S. Provisional Applications 60/805,697 and 60/805,669 filed Jun. 23, 2006 which are hereby incorporated herein by reference in their entirety.

STATEMENT REGARDING FEDERALLY SPONSORED RESEARCH OR DEVELOPMENT

This invention was made with United States Government support under Contract No. DTRS 56-02-T-0001 awarded by the U.S. Department of Transportation. The Government has certain rights in this invention.

FIELD OF THE INVENTION

This disclosure pertains to inspection of pipelines which may detect defects such as material-loss that may be present in a pipe wall. The inspection method and apparatus may also reduce in size or change shape and may pass through pipeline internal restrictions. The sensor module and/or exciter module on the apparatus may also expand and contract.

BACKGROUND

Remote-field eddy current (RFEC) sensing is a generally nondestructive testing method that may be used for inspecting pipelines. RFEC testing of pipelines may use an electromagnetic excitation coil driven by alternating current that may be positioned within a pipe. RFEC sensors may be located inside the pipe adjacent to the pipeline wall. The electromagnetic excitation coil and the sensors may typically be positioned at two axial locations in the pipe. The sensors may then be located in a remote field zone of the magnetic field produced by the coil. RFEC sensors may then detect a magnetic field that originated at the excitation coil, penetrated through the pipe wall to the outside diameter, and re-entered the pipe wall to the inside diameter at the sensor location. Since the magnetic field has penetrated the pipe wall, it may be affected by defects such as cracking or material loss on the inner diameter or outer diameter that may be present in the pipe wall.

SUMMARY

In a first exemplary embodiment, the present disclosure relates to a pipeline inspection device for a pipe. The inspection device may include an exciter coil capable of providing an alternating current magnetic field and producing eddy currents. A plurality of sensors may then be provided which are capable of sensing a magnetic field produced by the eddy currents and the sensors may be engaged with a sensor shoe. The sensors may then be capable of being positioned at a first radial distance $D_1$ with respect to an inner pipe wall surface and capable of providing coupling to the magnetic field produced by the eddy currents. The sensor shoe may also be capable of retracting to a second radial distance $D_2$, wherein $D_1 < D_2$. The sensor shoe may be connected to a sensor support arm wherein the support arm may be pivotably attached to a fixed hub and to a control arm, which control arm may be pivotably attached to a driven hub.

In method form, the present disclosure relates to a method of inspecting a pipe comprising providing an exciter coil capable of providing an alternating current magnetic field and producing eddy currents. One may then provide one or a plurality of sensors capable of sensing a magnetic field produced by the eddy currents wherein the sensors may be engaged with a sensor shoe. One may then position the sensor shoe at a first radial distance $D_1$ with respect to an inner pipe wall surface to provide coupling to the magnetic field produced by the eddy currents, followed by sensing the magnetic field produced by the eddy currents. One may then retract the sensor shoe to a second radial distance $D_2$, wherein $D_1 < D_2$.

BRIEF DESCRIPTION OF THE DRAWINGS

The detailed description below may be better understood with reference to the accompanying figures which are provided for illustrative purposes and are not to be considered as limiting any aspect of the invention.

DETAILED DESCRIPTION

Figure 1A:
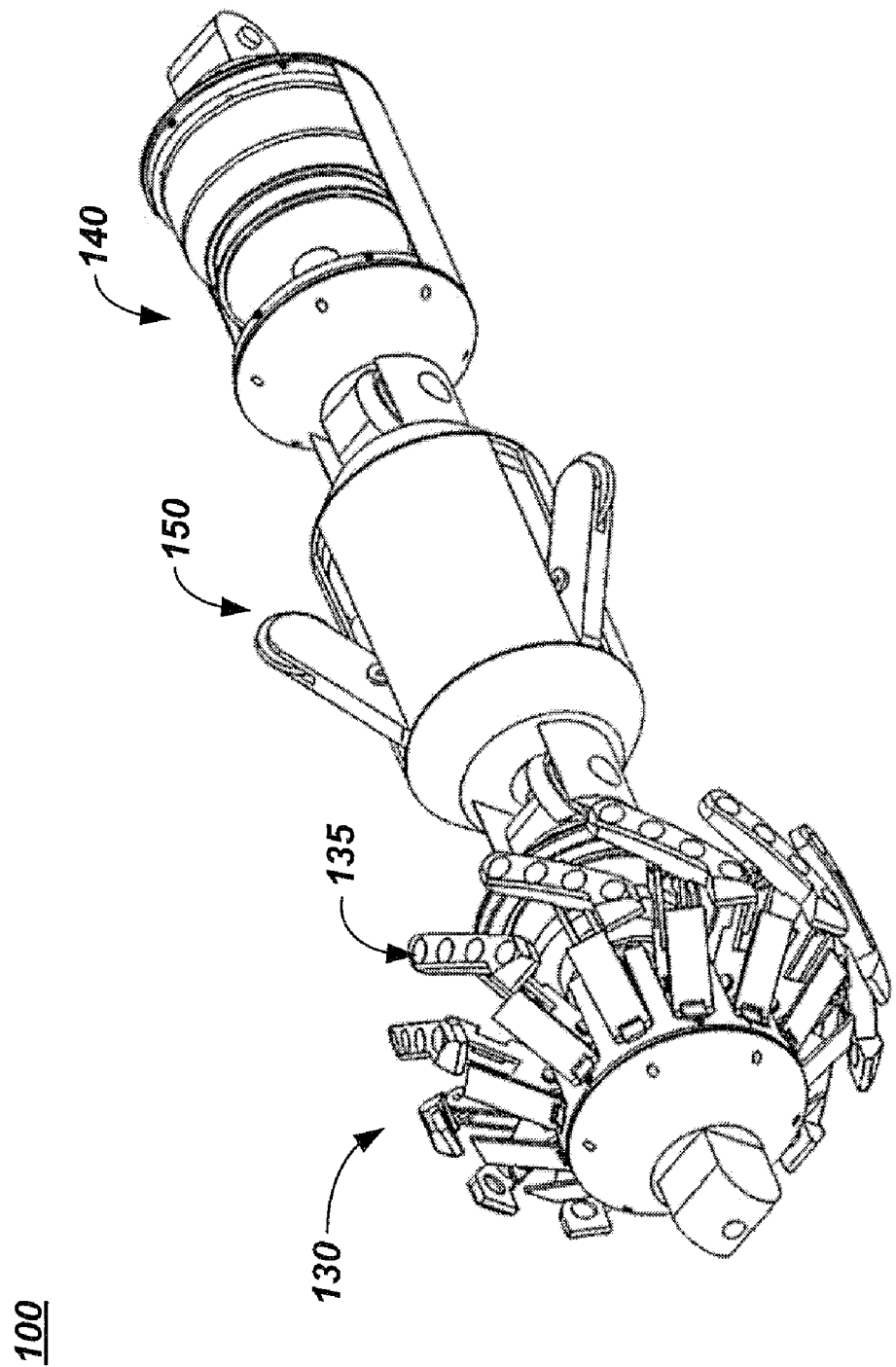
FIGS. 1A and 1B depict an exemplary system embodiment of a sensor module and a fixed diameter exciter module in an expanded view and a retracted view, respectively.
Figure 1B:
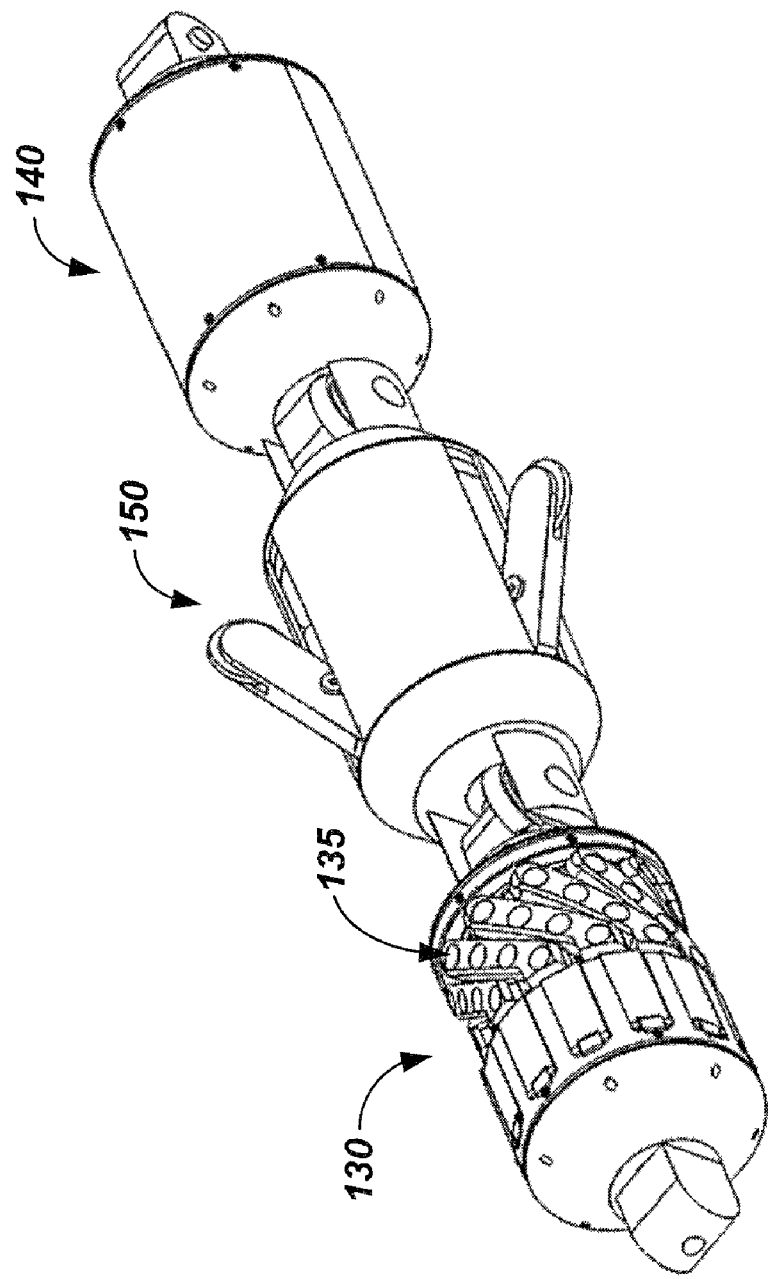

Attention is directed to FIGS. 1A and 1B which illustrate an exemplary embodiment of the disclosed RFEC pipe inspection system 100 in an expanded view and a retracted view, respectively. The RFEC pipe inspection system 100 may include an exciter module 140 and a sensor module 130. A cover (not shown) of the exciter module 140 has been removed in FIG. 1A for clarity. These modules 130, 140 may be integrated with a support module 150 that may maintain the connected modules positioned substantially within the pipe, e.g., at about the center of the pipe. The exciter module 140 may generate an AC magnetic field that may create the flow of eddy currents in a pipe wall. The sensor module 130 may contain one or a plurality of sensors 135 that may be used to detect the magnetic field that may be generated by the eddy currents in the pipe wall, providing a capability to detect defects (e.g., material loss or cracking) that may be present in the pipe wall that may interrupt the eddy current flow. The modules 130, 140, 150 may be designed to expand during inspection and retract as necessary to traverse bends or obstacles in the pipe.

Figure 2A:
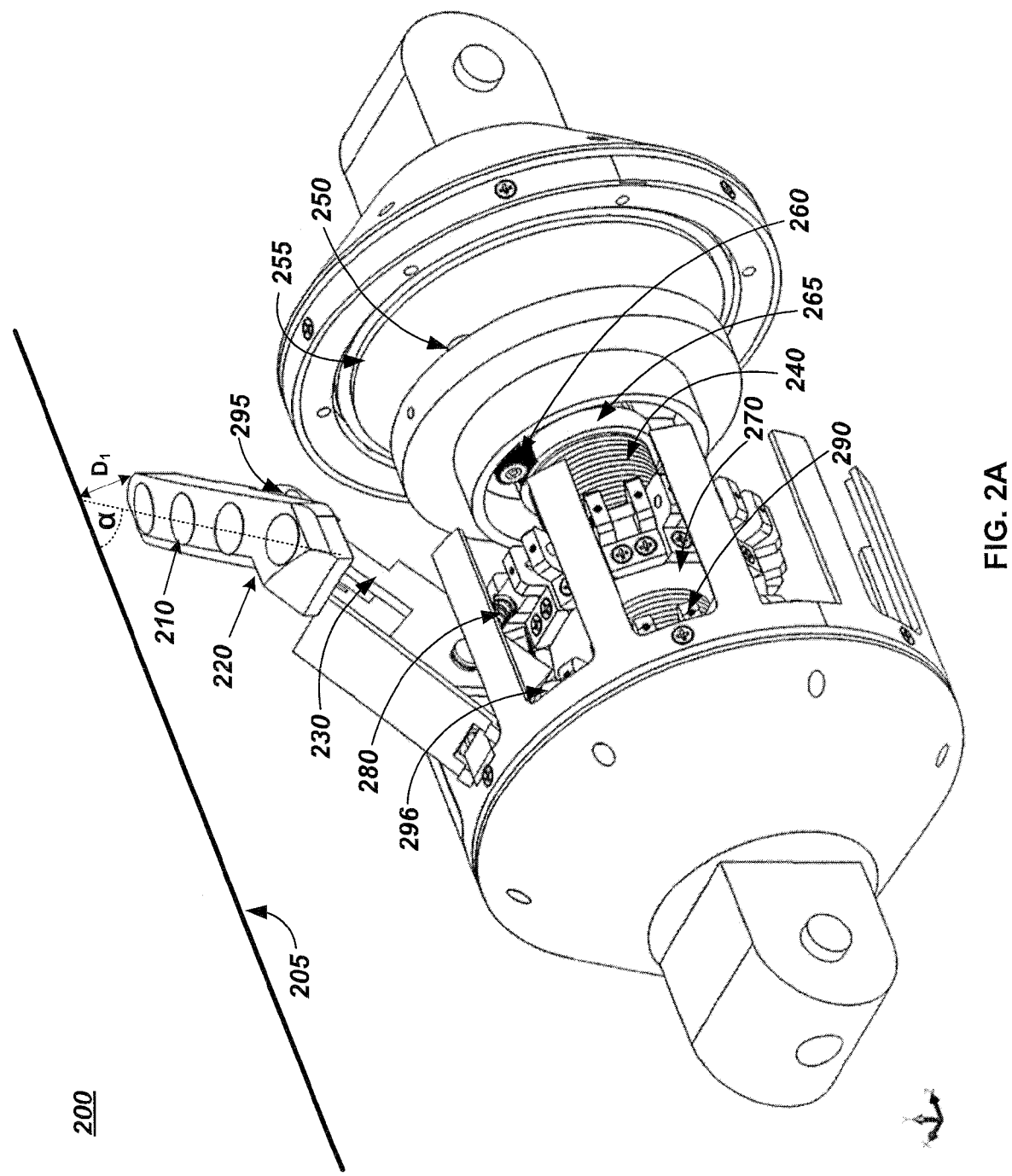
FIGS. 2A and 2B depict exemplary views of sensor modules depicting two exemplary sensor arm configurations and showing only a single sensor support arm for clarity.

Attention is directed to FIG. 2A that illustrates a further view of an exemplary sensor module 200 depicting only a single exemplary sensor support arm 230 and control arm 280 for clarity. As noted above, the sensor module 200 may contain one or a plurality of sensors 210 disposed in or on one or more sensor shoes 220 that may be deployed by one or more sensor support arms 230. A shoe herein may therefore be understood as a structure that engages one or more sensors and which may support or position a sensor against a pipe inner surface. The sensors 210 may be oriented to detect a component of the magnetic field. As illustrated, the sensor shoe surface may be positioned at a distance $D_1$ from the inner pipe wall surface.

In addition, the intersection of the magnetic field with a sensor 210 may take place at a number of angles, depending upon how the sensor shoe 220 and/or sensors 210 are orientated with respect to the inner pipe wall 205. As illustrated, a centerline of the sensor shoe 220 may be positioned at an angle α formed by the intersection of the centerline of the shoe with the axial axis of the pipe. Such angle may be about 0 degrees to about 90 degrees, including all values and increments therein. For example, the angle α may be about 30-60 degrees. Such position may provide more detailed sensing of defects that may appear in the pipe. Using a plurality of sensors 210, inspection data may be obtained from all or a portion of the entire circumference of the pipe with a single pass of an inspection device through the pipe.

It may therefore be appreciated herein that in order to pass through a given obstruction within the pipe, the sensor shoes 220 and sensor support arms 230 may retract. Such retraction may vary and may include a level of retraction sufficient such that the sensor shoes 220 and support arms 230 may be configured to fit within a largest diameter component of the module 200. The diameter of the sensor module 200 is shown as item "D" in FIG. 3. When the module 200 is configured for further inspection, the sensor shoes 220 and support arms 230 may be extended as desired. The sensor module 200 may contain electronic circuitry to support functions of the inspection device such as signal generation, signal reception and processing, communications with the transport vehicle and operator, and control of the deployment and retraction operation. The circuitry may be located on printed circuit boards, such as printed circuit board 255, within the sensor module 200.

The sensor module 200 may therefore contain a mechanism for deploying and retracting the sensor shoes 220. For example, a motor 250 and gears 260, 265, or other mechanical mechanism may be used to rotate a lead screw 240 or other advancement mechanism, which may move a driven hub 270 in a direction that may be substantially parallel to the axial axis of the module 200. This driven hub 270 may be pivotably connected to the sensor support arms 230 by a control arm, for example, a compliant strut 280. Reference to compliant is reference to a feature that may provide a force in response to a stress, e.g. a spring. One portion of a sensor support arm 230 may be connected to a fixed hub 290 by a pivoting joint 296. Reference to a fixed hub therefore may be understood as any non-moving structure capable of pivotably connecting the sensor support arm and which may pivotably connect to a plurality of support arms. A sensor shoe 220 may be connected to another portion of a sensor support arm 230 by a pivoting joint 295. As the lead screw 240 rotates, a sensor shoe 220 may move to a different radial distance from the axial centerline of the module 200. This radial movement may allow the module 200 size to be adjusted which may assist traversing pipe restrictions and/or it may also accommodate different pipe diameters.

Figure 2B:
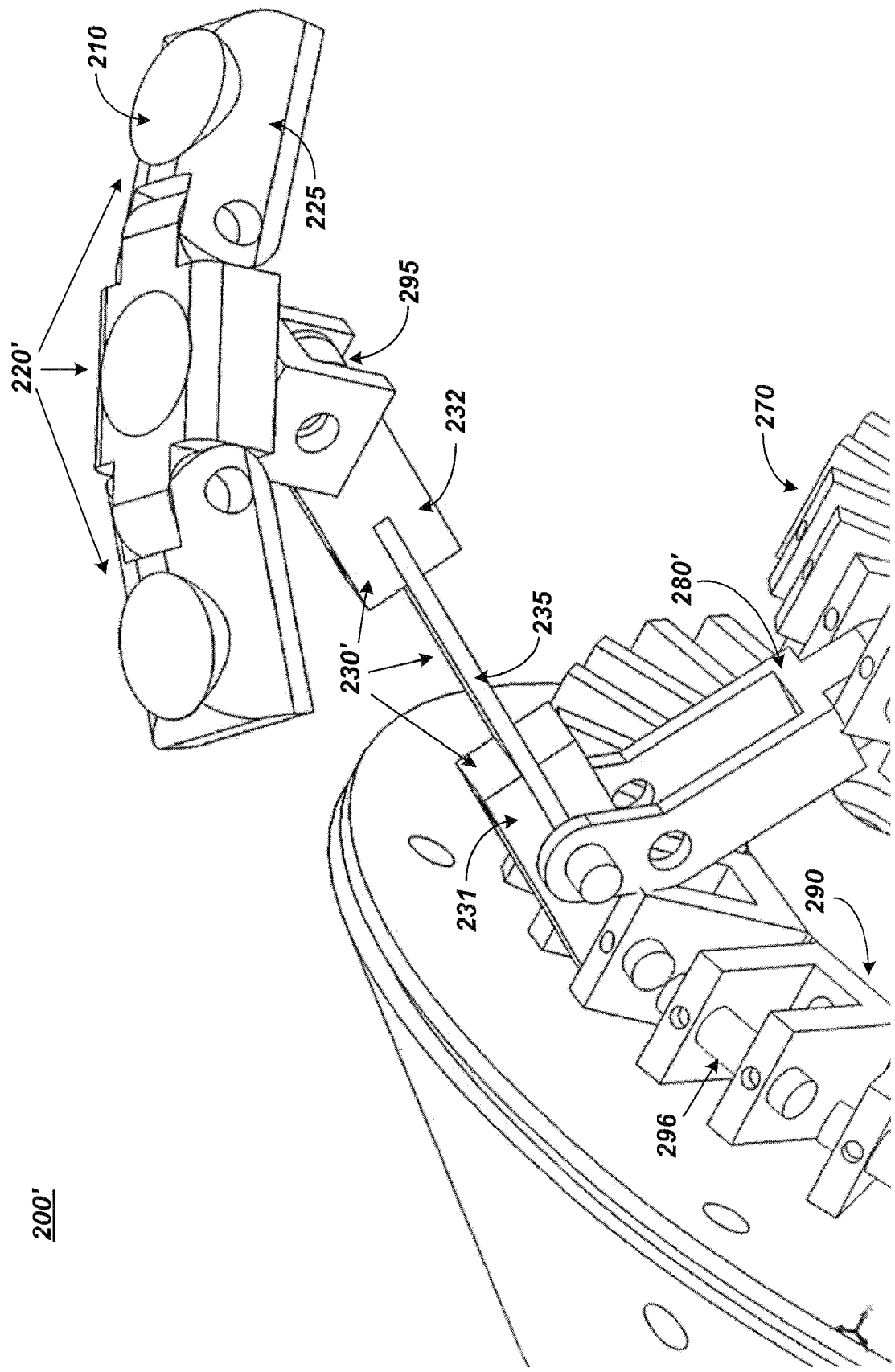

Attention is directed to FIG. 2B which illustrates a portion of another exemplary embodiment of a sensor module 200' depicting only a single sensor shoe 220' (for clarity), sensor support arm 230' and control arm 280' for clarity. It may now be appreciated that a control arm may be understood as any structure that may provide a force which may ultimately cause extension or retraction of the sensor shoe 220'. In addition, as can now be seen, the illustrated control arm 280' may be connected to the driven hub 270, which may move axially so that the control arm may function as described. Reference to a driven hub may therefore be understood as reference to any component which may move in a selected direction to introduce movement to the control arm 280'.

Sensor support arm 230' may be formed from components 231, 232 and 235. Component 231 of the sensor arm 230' may then be pivotably connected to fixed hub 290 and pivotably connected to control arm 280'. Furthermore, component 232 of the sensor arm 230' may be pivotably connected at 295 to the sensor shoe 220'. In addition, it is worth noting that component 235 may specifically amount to a leaf-spring. It may therefore be appreciated that component 235 may deflect as the sensor shoe 220' may contact a pipe wall. It may be further appreciated that as the driven hub 270 moves axially by rotation of the lead screw 240 (FIG. 2A) the sensor shoe 220' may be biased (i.e. flexibly positioned) against the pipe wall by component 235. The sensor shoe 220' may include segments 225 wherein each segment 225 may contain at least one sensor 210.

Figure 3:
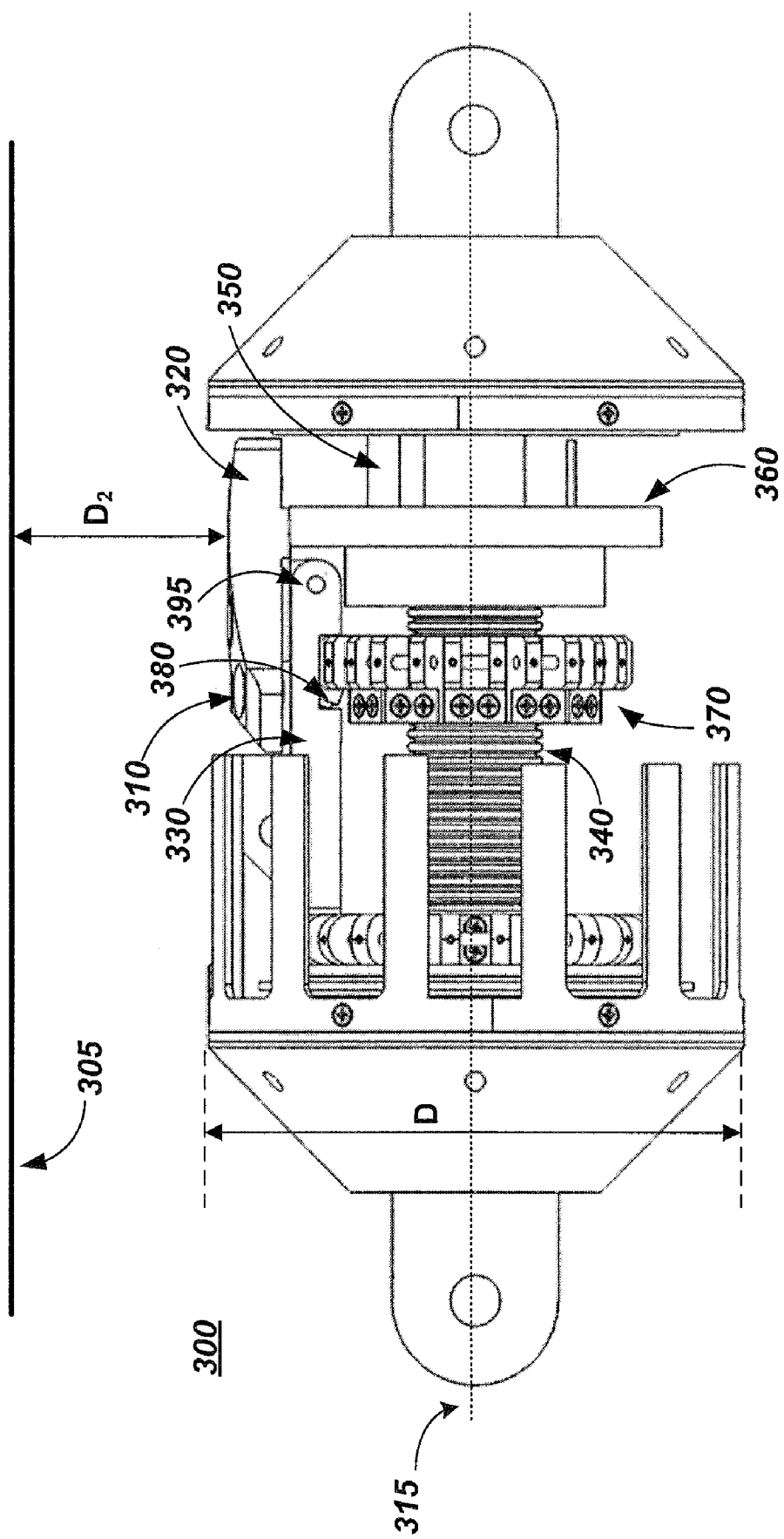
FIG. 3 shows a side view of an exemplary sensor module in a retracted position depicting only a single sensor support arm for clarity.

Attention is directed to FIG. 3 which illustrates a side view of an exemplary sensor module 300 of the pipeline inspection device in one potential retracted position depicting only a single exemplary sensor support arm 330 for clarity. The pipeline inspection device may have an axial axis 315. Similar to the above, in operation, a lead screw 340 or other advancement mechanism may be rotated by a motor 350. A lead screw may therefore be understood as a threaded rod or other structure which may rotate to advance the driven hub. Accordingly, the lead screw 340 may move a sensor shoe 320 outward radially until the shoe 320 contacts an inner pipe wall 305. The shoe 320 may again pivot at its attachment 395 to a sensor arm 330. The shoe 320 may eventually align itself so that it may be near or in contact with the inner pipe wall 305 along the length of the shoe 320. Once the shoe 320 is aligned, the movement may be continued until a spring-loaded strut 380 may be partially compressed or a leaf spring 235 may be deflected. This may allow the shoe 320 to be spring-loaded with a desired force against the pipe wall 305. It may also allow the shoe 320 to track the pipe wall 305 even though the sensor module 300 radial position may vary as the inspection device itself is transported along the pipe. This then may also allow the sensor shoe 320 to pass over imperfections in the inner diameter of the pipe wall (e.g. weld protrusions) while maintaining contact with the pipe wall 305. Accordingly, it may be appreciated that the sensor module may not be positioned along the centerline of the pipe while the shoes 320 and accompanying sensors 310 may remain at a location suitable to provide adequate coupling.

By reversing the rotation of the lead screw 340, the sensor shoe 320 may be retracted until it reaches its fully retracted position or an intermediate position. In the retracted position, the sensor arm 330 may contact a driven hub 370 and the sensor shoe 320 may contact a rear fixed hub 360. This may provide mechanical support for any loads that may be applied to the sensor shoe 320, particularly as the module 300 may move around bends or other restrictions or obstructions in the pipe.

Figure 4A:
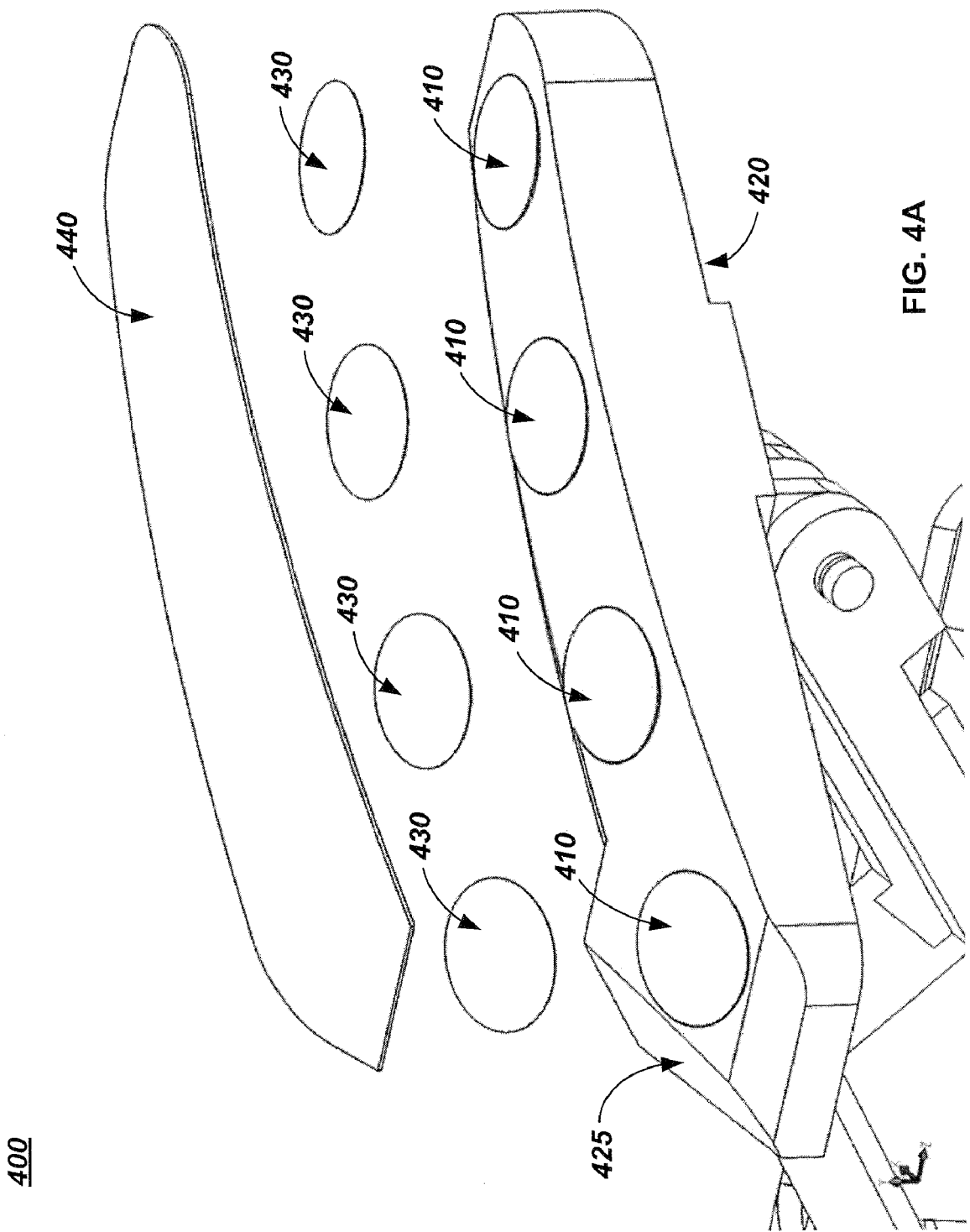
FIGS. 4A and 4B show exemplary embodiments of sensor shoe configurations.

Attention is directed to FIG. 4A which illustrates an exemplary embodiment of a sensor shoe configuration 400. As alluded to above, each sensor shoe 420 may contain one or more sensors 410. The shoe 420 may be shaped with a curvature similar to that of the curvature provided by the inner pipe wall. For example, the shoe 420 may assume a curvature to ensure that the sensors 410 on the shoe may be sufficiently close to the inner pipe wall diameter to provide coupling between the sensors 410 and the magnetic field.

Figure 4B:
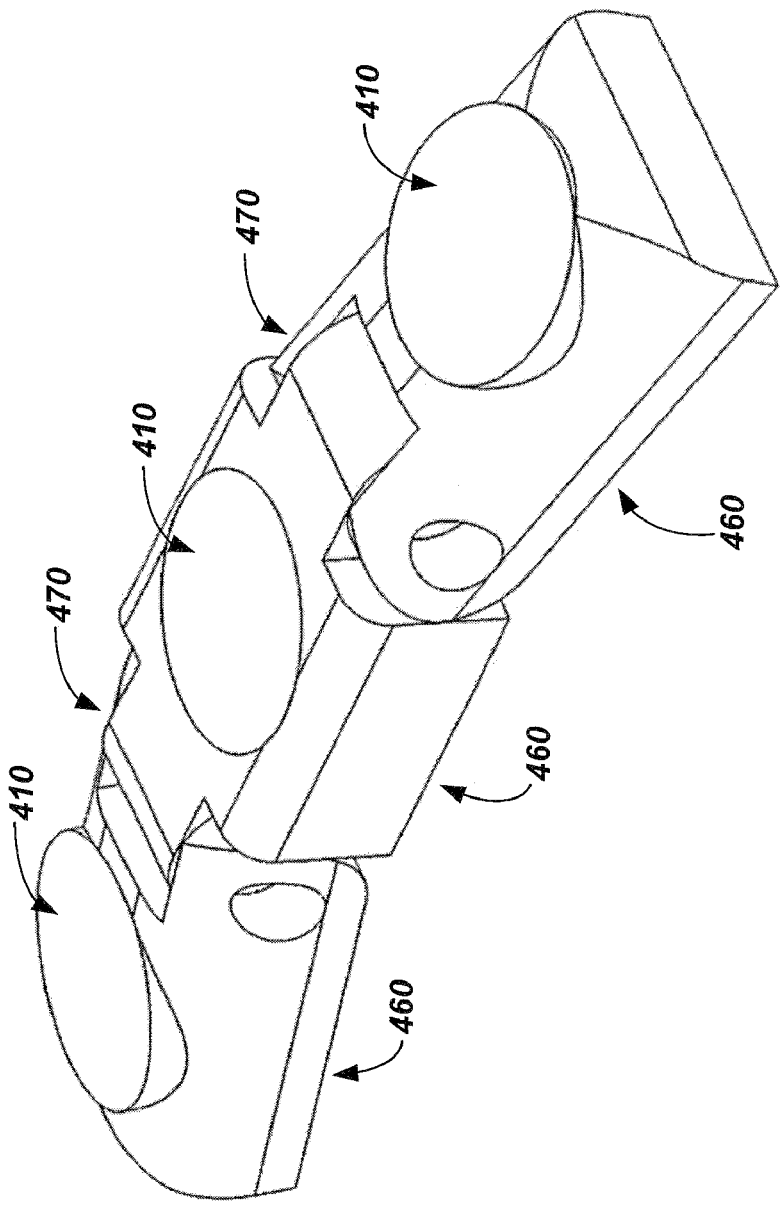

In addition, as shown in FIG. 4B, the sensor shoe 450 may itself contain segments. Each segment 460 may include an individual sensor 410. Each segment 460 may be coupled to an adjacent segment 460 by an articulating joint 470. Each individual segment 460 may articulate relative to another segment 460. In this manner, each individual sensor 410 may respond individually to the inner pipe wall when traveling down the length of the pipe and again, may be sufficiently close to the inner pipe wall surface to provide coupling to the applied magnetic field.

As shown in FIG. 4A, for example, the front 425 of the shoe 420 may have a beveled or rounded edge. This alignment mechanism, along with the beveled shoe edge, may allow the shoe 420 to ride up and over small protrusions on the pipe wall, such as from girth welds, as the inspection device travels along a pipe. The sensors 410 may be installed in the shoe 420 with a protective wear-resistant covering on the outside of the shoe 420. The wear-resistant covering may comprise a first layer 430 installed over each sensor 410 and/or a second layer 440 installed over the shoe 420 and the first layer 430. The second layer 440 may comprise a relatively low-friction surface, such as those materials that may provide a static or kinetic coefficient of friction (COF) of less than or equal to about 0.50. For example, layer 440 may include a thermoplastic material such as polyethylene, which may provide a COF of less than or equal to about 0.25. The first layer 430 may include a material that provides a back-up wear resistance to layer 440 and may specifically include materials with a higher hardness than the first layer 430, which relatively higher hardness may therefore provide resistance to puncture. For example, the materials for layer 440 may have a hardness on the Rockwell C scale or higher. Suitable materials therefore include ceramics, which may be understood as an inorganic material with a compressive strength of greater than about 40,000 psi. The shoe 420 may itself be formed from a polymer resin that may include filler material. For example, the shoe may be formed from a polyurethane resin containing inorganic filler, e.g., glass and/or aluminum oxide. The shoe itself may therefore have a hardness of greater than about 50 D, with a tensile strength of greater than about 8500 psi, a tensile modulus of greater than about 200,000 psi, and a flexural modulus of greater than about 300,000 psi.

Figure 5A:
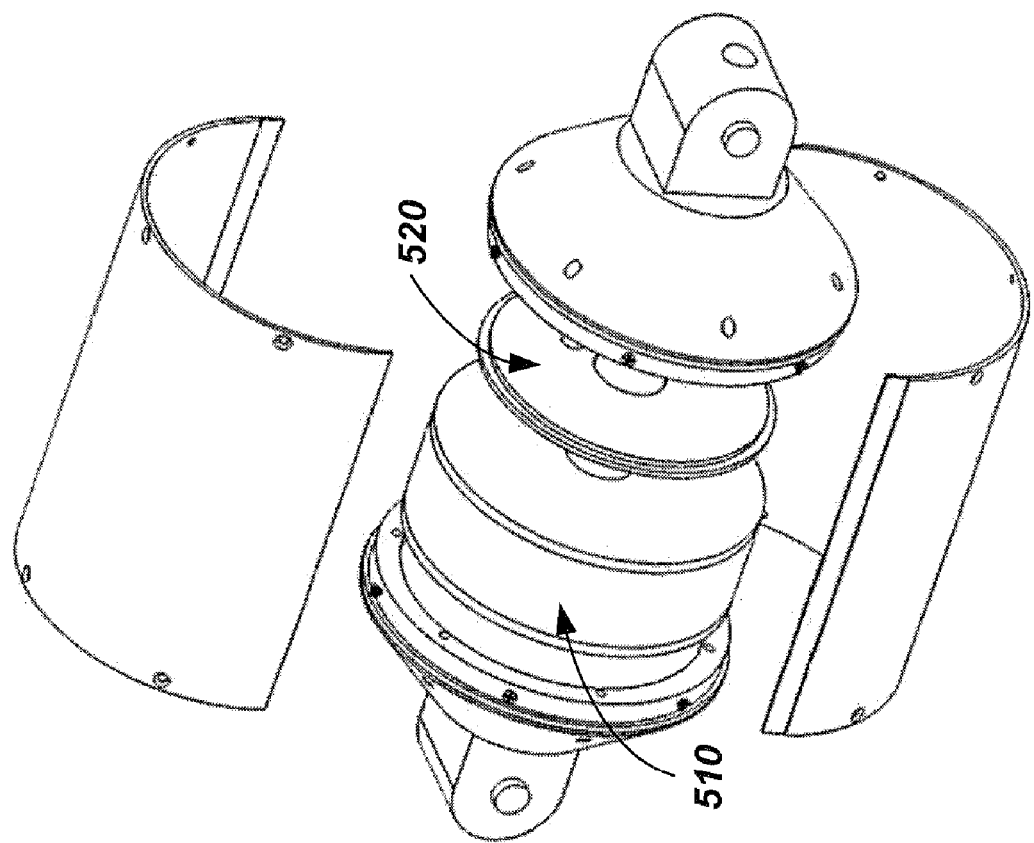
FIG. 5A shows an exemplary exciter module with a fixed diameter exciter coil.

Attention is directed to FIG. 5A which illustrates an exemplary exciter module 500 with an exemplary fixed diameter exciter coil 510. A fixed diameter coil may be understood as an electromagnetic coil wherein the diameter of the coil remains constant. The exciter module 500 may contain the RFEC exciter coil 510 and may contain electronic circuitry on a printed circuit board 520. The module 500 may connect to adjacent modules such as a sensor module or a support module, as shown, for example, in FIGS. 1A, 1B, 6, 7 and 8. The exciter coil 510 may be of a fixed or variable diameter (see below) and may be sufficiently small so that it may pass through obstacles without the need to retract to a smaller diameter, for example, as shown in FIG. 5A. It is also worth noting that the exciter coil 510 may be at least two pipe diameters in distance from that sensor 410 that may be closest in axial distance to the coil 510.

Figure 5B:
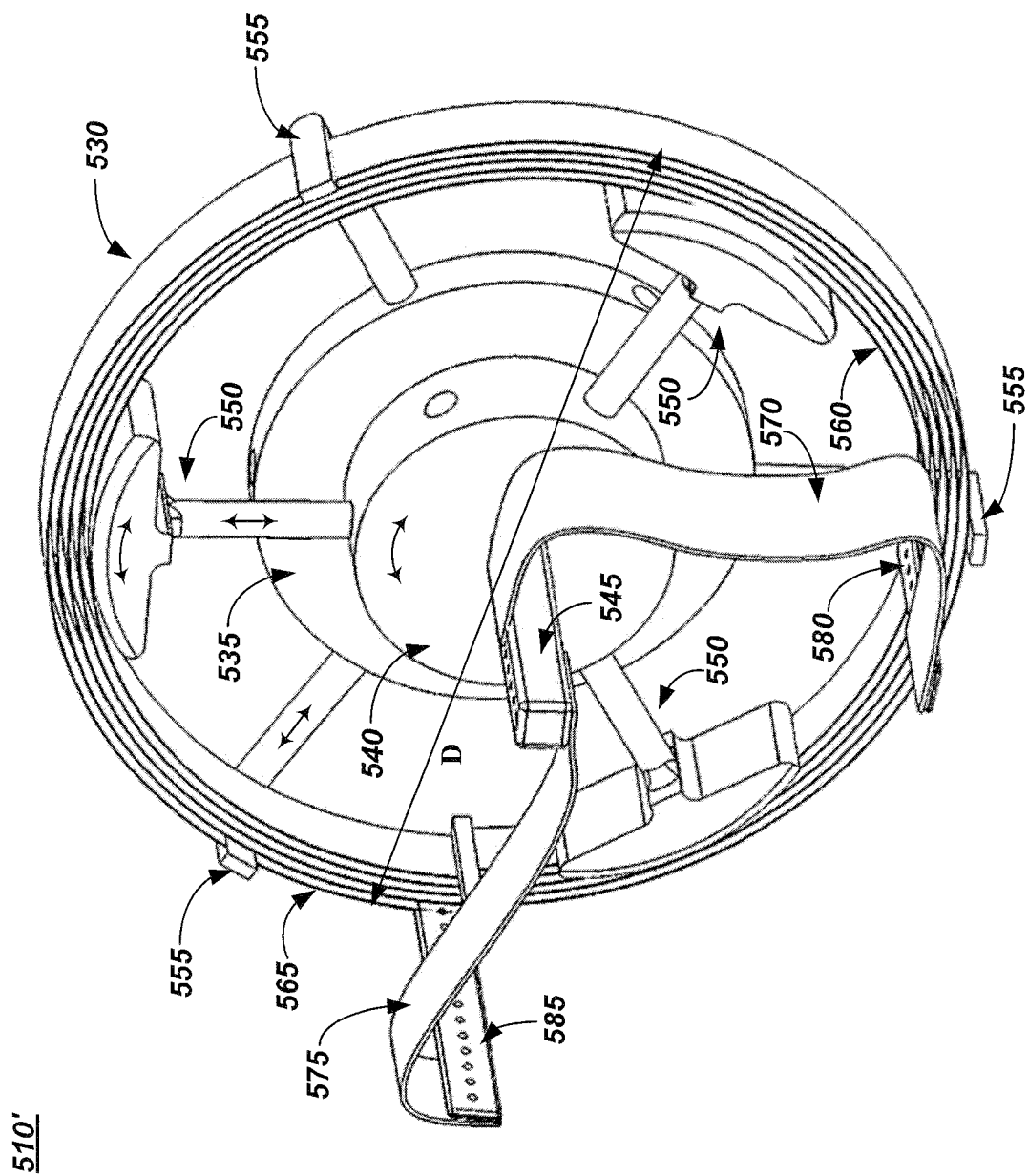
FIGS. 5B and 5C show an exemplary variable diameter exciter coil at an increased and a reduced diameter, respectively.

Attention is directed to FIG. 5B which illustrates an exemplary exciter coil 510' that may provide a variable diameter. The variable diameter coils herein include those variable diameter coils disclosed in U.S. Application 60/805,669 filed Jun. 23, 2006 whose teachings are incorporated by reference. In addition, the variable diameter coils herein include those variable diameter coils disclosed in U.S. Pat. No. 7,154,264, whose teachings are also incorporated by reference. The variable diameter may therefore allow the coil 510' to expand or contract in a radial direction. For example, in the case of a given pipe inspection, the coil 510' may contract to traverse a pipe restriction and may then expand. The coil 510' may be operational at any diameter D within its range of diameters. Thus, the coil 510' may be sized to fit pipes of various diameters.

The exciter coil 510' may include a coil winding 530, a deployment mechanism and capability for external electrical connections. The coil winding 530 may include one or a plurality of conductors arranged in a manner that may be similar to aspects of a ribbon cable. In other words, the conductors may be arranged in a parallel, substantially coplanar configuration, and may be surrounded and/or separated by an insulating material. The coil winding 530 may be wound in a manner similar to aspects of a clock spring. In other words, the diameter D of the coil 510' may decrease as the coil winding 530 is wound and the diameter D may increase as the coil winding 530 is unwound.

The deployment mechanism may include a fixed hub 535, a rotatable hub 540, one or more inner supports 550, and one or more outer supports 555. An inner support 550 may be connected to an inner winding layer 560 and an outer support 555 may be connected to an outer winding layer 565. The inner supports 550 and the outer supports 555 may extend and retract in the radial direction as the rotatable hub 540 may be rotated. The inner supports 550 may also rotate along with the rotatable hub 540. The supports 550, 555 may be configured to extend or retract in proportion to the rotation of the rotatable hub 540.

An inner support 550 may be connected to the inner winding layer 560 and may be configured to move the inner winding layer 560 in a rotational direction. An outer support 555 (which may move in and out radially) may be connected to the outer winding layer 565 and may fix the outer winding layer 565. As the inner supports 550 rotate, the inner supports 550 and the outer supports 555 may move in the radial direction in proportion to the rotation of the rotatable hub 540. As depicted in FIG. 5B, rotation of the rotatable hub 540 in the clockwise direction may cause a decrease in coil diameter D while rotation in the counterclockwise direction may cause an increase in coil diameter D.

An interconnect hub 545, that may not rotate, may provide for electrical connection between the coil winding 530 and an external power source (not shown). The interconnect hub 545 may be connected to an inner interconnect cable 570 and an outer interconnect cable 575. The inner interconnect cable 570 may be further connected to an end of the inner winding layer 560 via an inner connector 580 and the outer interconnect cable 575 may be further connected to an end of the outer winding layer 565 via an outer connector 585. As the diameter D of the coil 510' may decrease, the inner interconnect cable 570 may be wound about the interconnect hub 545. As the diameter D of the coil 510' may increase, the inner interconnect cable 570 may be unwound. The outer interconnect cable 575 may not wind about the interconnect hub 545.

Figure 5C:
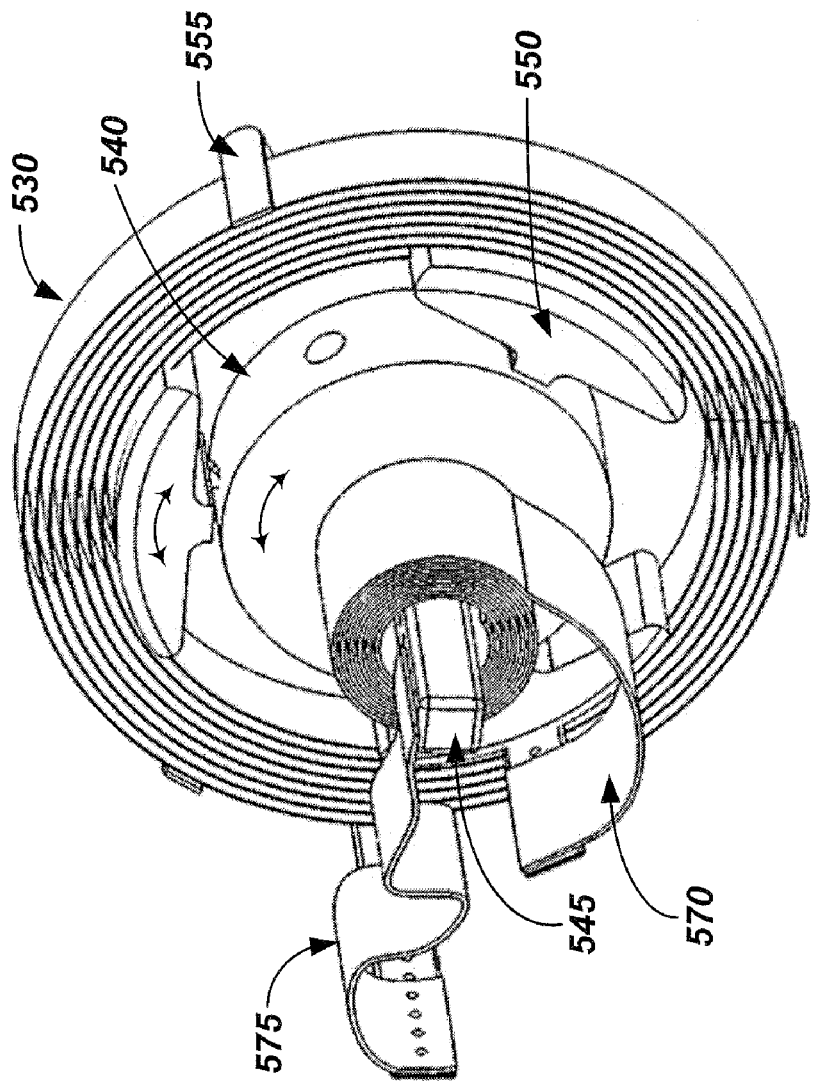

Attention is directed to FIG. 5C which illustrates an exemplary variable diameter excitation coil 510' at a reduced diameter. As illustrated, the inner interconnect cable 570 may be wound about the interconnect hub 545 and the inner and outer supports 550, 555 may be retracted.

Figure 6:
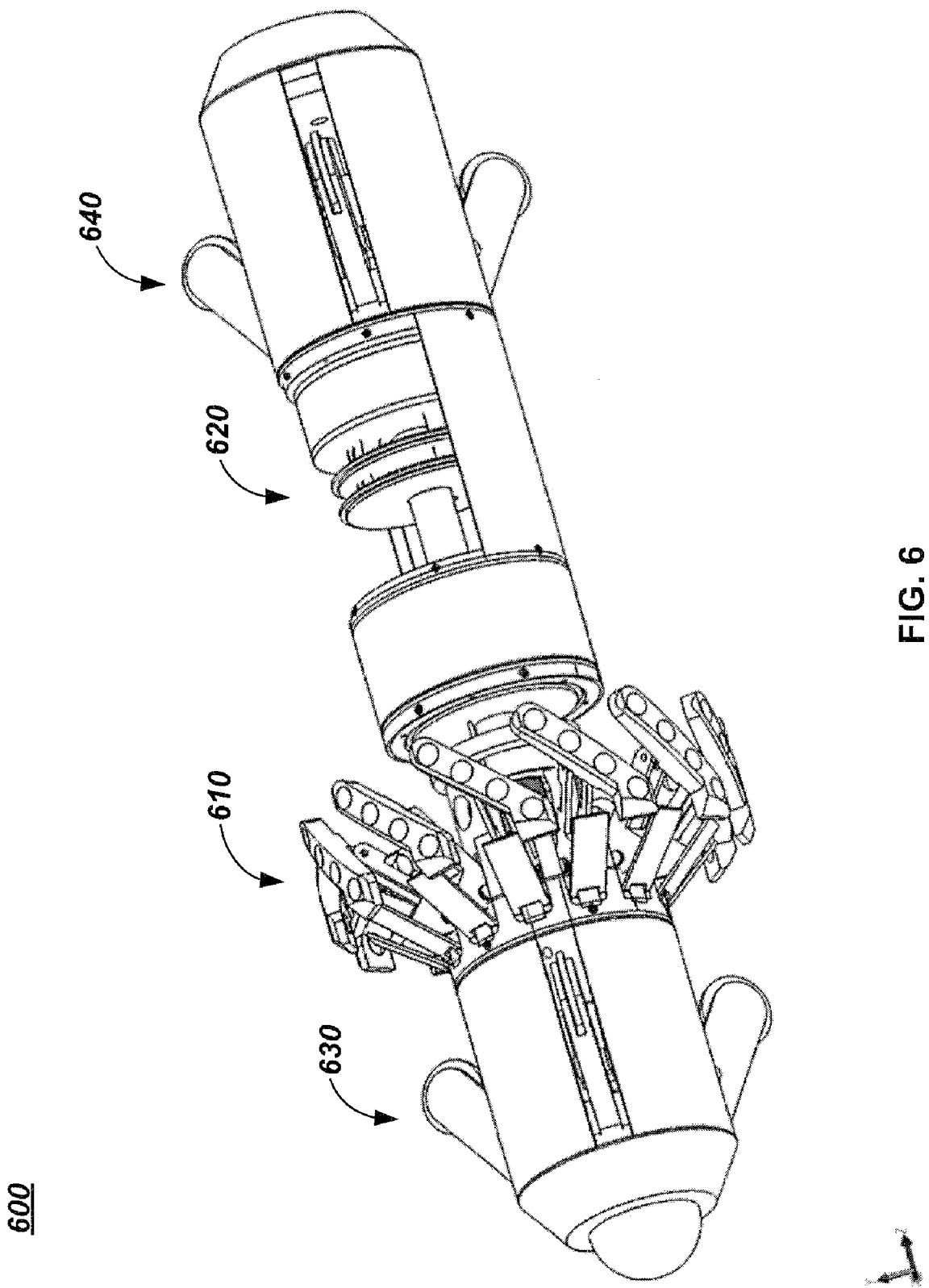
FIG. 6 shows an exemplary system transport embodiment of an expanded exemplary sensor module and an exemplary fixed diameter exciter module configured in a single rigid body.

Attention is next directed to FIG. 6 which illustrates an exemplary transport system 600 including an exemplary expanded sensor module 610 and an exemplary exciter module 620. The transport system 600 may be configured as a single relatively rigid transport embodiment 600 further including an exemplary front support module 630 and an exemplary rear support module 640. Reference to rigid is reference to the feature that the transport system does not substantially flex relative to the axial direction by more than about +/−5.0 degrees with respect to a center axial axis. One cover of the exciter module 620 has been removed for clarity. The support modules 630, 640 may position the transport system 600 in a pipe (not shown) and may propel the transport system 600 along the pipe.

Figure 7:
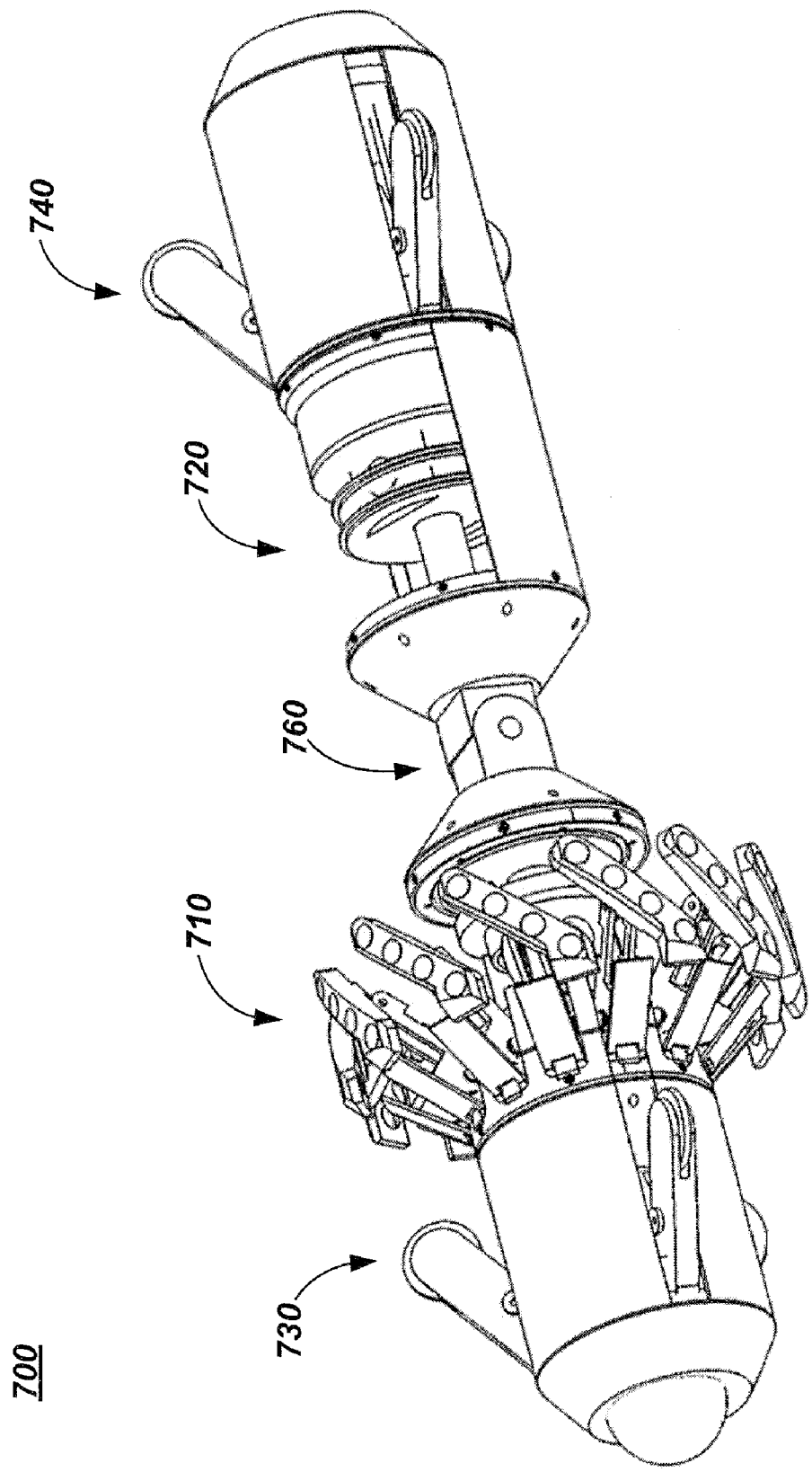
FIG. 7 shows an exemplary system transport embodiment of an exemplary expanded sensor module and an exemplary fixed diameter exciter module configured in a single segmented body.

Attention is directed to FIG. 7 which illustrates another exemplary transport system 700 including an expanded exemplary sensor module 710 and an exemplary fixed diameter exciter module 720. The transport system may be configured as a segmented transport embodiment 700, wherein the sensor module 710 and the exciter module 720 may be flexibly coupled by a joint 760. As may be appreciated, the joint 760 may provide articulation of the exciter module 720 relative to the sensor module 710. Such articulation may include a flex relative to the axial axis of, e.g., +/−90 degrees, including all values and increment therein. A cover of the exciter module 720 has been removed for clarity. A front support module 730 may be rigidly connected to the sensor module 710, and a rear support module 740 may be rigidly connected to the exciter module 720. The support modules 730, 740 may position the sensor module 710 and the exciter module 720 in a pipe (not shown) and may propel the transport system 700 along the pipe.

Figure 8:
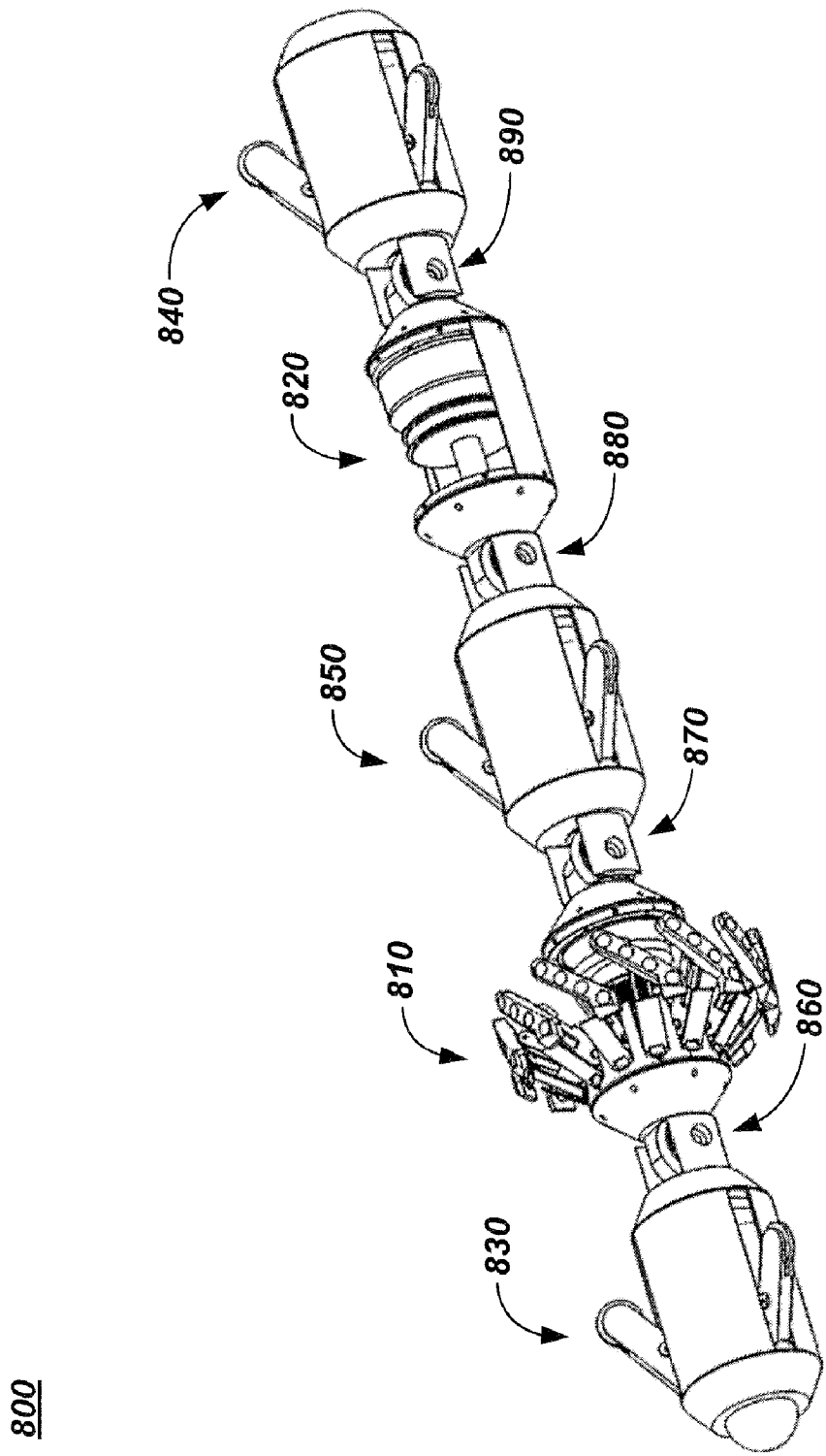
FIG. 8 shows an exemplary system transport embodiment of an exemplary expanded sensor module and an exemplary fixed diameter exciter module configured in a multiple segmented body.

Attention is directed to FIG. 8 which illustrates yet another exemplary embodiment of a transport system 800 including an expanded exemplary sensor module 810 and an exemplary fixed diameter exciter module 820 that may be configured in a multiple segmented transport system 800. A cover of the exciter module 820 has been removed for clarity. A front support module 830 may be flexibly connected to a front location on the sensor module 810 by a joint 860, and the sensor module 810 may be flexibly connected to a front location on an intermediate support module 850 by flexible joint 870, that may be located at a rear position of the sensor module 810. The intermediate support module 850 may be flexibly connected to a front location of the exciter module 820 by a joint 880, connected at a rear location on the intermediate support module 850. A rear support module 840 may be flexibly connected to the exciter module 820 by a joint 890, at a rear location on the exciter module 820. The support modules 830, 840, 850 may position the sensor module 810 and the exciter module 820 in the pipe (not shown) and may propel the transport system 800 along the pipe.

Figure 9:
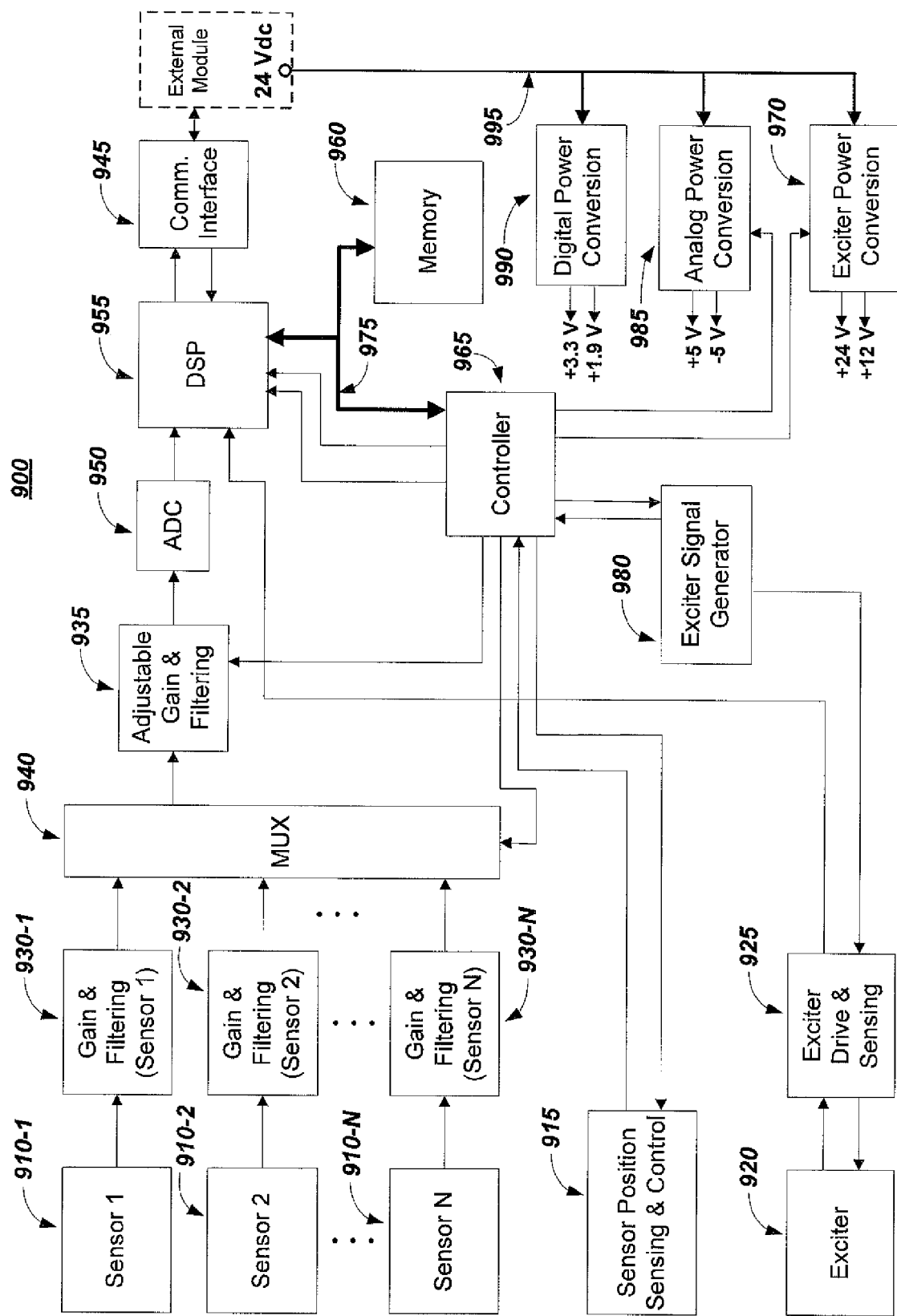
FIG. 9 shows an exemplary electronic circuit block diagram for a sensor module and exciter module.

Attention is directed to FIG. 9 which illustrates an exemplary electronic circuit 900 block diagram for an exemplary sensor module and an exemplary exciter module. An output of each of a plurality of sensors 910 may be connected to an input of each of a plurality of gain and filtering stages 930. An output of each of the plurality of gain and filtering stages 930 may be connected to an input of a multiplexer (MUX) 940. An output of the MUX 940 may be connected to an input of an adjustable gain and filtering stage 935. An output of the adjustable gain and filtering stage 935 may be connected to an input of an analog to digital converter (ADC) 950. An output of the ADC 950 may be connected to an input of a digital signal processor (DSP) 955.

An output of a controller 965 may be connected to the MUX 940. An output of the controller 965 may be connected to the adjustable gain and filtering stage 935. One or more outputs of the controller 965 may be connected to the DSP 955. An input and an output of the controller 965 may be connected to a sensor position sensing and control stage 915. An input and an output of the controller 965 may be connected to an exciter signal generator 980. Outputs of the controller 965 may be connected to an exciter power conversion stage 970 and an analog power conversion stage 985. The controller 965 may be further connected to a bus 975. The bus 975 may be further connected to a memory stage 960 and to the DSP 955. Memory 960 may include both data memory and boot memory. The DSP 955 may be further connected to a communications interface stage 945. An exciter drive and sensing stage 925 may be connected to an exciter 920, to an input of the DSP 955 and to an output of the exciter signal generator 980. A power supply bus is shown at 995 which may supply power, for example 24 Vdc, to the system. The power supply bus 995 may be connected to a digital power conversion stage 990, the exciter power conversion stage 970 and the analog power conversion stage 985.

Each sensor 910-$n$ may sense a component of a magnetic field (not shown) and may output a signal representative of the sensed magnetic field component. The output signal of each sensor 910-$n$ may be amplified and filtered by a gain and filtering stage 930-$n$ and the amplified and filtered signal may be input to the MUX 940. The MUX 940 may be controlled by the controller 965, to select for output, one of the amplified and filtered signals representative of a sensed magnetic field component. The signal representative of a sensed magnetic field component may be further amplified and filtered by adjustable gain and filtering stage 935. The magnitude of amplification may be controlled by the controller 965. The selected signal representative of a sensed magnetic field component may be digitized by the ADC 950 and the digitized signal may be processed by the DSP 955.

The DSP 955 may perform a lock-in amplifier function (phase sensitive detection) on the digital signal representative of a sensed magnetic field component. The exciter signal generator 980 may provide a synchronization signal to the controller 965. The controller 965 may use the synchronization signal from the exciter signal generator 980 to provide an exciter phase reference signal to the DSP 955 that may be used to synchronize the lock-in amplifier function. The DSP 955 may generate, as an output of the lock-in amplifier function, an in-phase component and a quadrature component of the digital signal representative of a sensed magnetic field component. The in-phase and quadrature components may be stored in memory 960 via bus 975.

The exciter signal generator 980 may receive an exciter drive control signal from the controller 965 and may provide an exciter drive signal to the exciter drive and sensing stage 925. The exciter signal generator 980 may include a direct digital synthesizer that may provide an analog output signal in response to the drive control signal from the controller 965. The exciter drive and sensing stage 925 may amplify the exciter drive signal using, for example, a power amplifier, and may provide the amplified exciter drive signal to the exciter 920. The exciter drive and sensing stage 925 may also sense exciter 920 current and may provide a signal representative of the exciter 920 current to the DSP 955. The signal representative of the exciter 920 current may be digitized prior to being received by the DSP 955, for example, by an analog to digital converter (not shown) or the analog to digital conversion may be performed by the DSP 955.

Sensor 910 position may be detected by a sensor position sensing and control stage 915. Sensor 910 position data may be provided to the controller 965 by the sensor position and control stage 915. The controller 965 may provide a sensor position control signal to the sensor position sensing and control stage 915. The sensor position and control stage 915 may control a drive motor (not shown), based on the sensor position control signal to adjust the position of the sensors 910.

The controller 965 may provide a sample trigger signal to the DSP 955. The DSP 955 may receive and process a digital signal representative of a sensed magnetic field component in response to the sample trigger signal. The controller 965 may control the analog and exciter power conversion stages 985, 970 to cause them to go to a low power state.

The DSP 955 may communicate with an external transport or support module (not shown) via the communication interface 945. The communication interface 945 may provide electrical isolation between the DSP 955 and the external transport or support module. The communication interface 945 may be a CAN bus, for example, or some other communication protocol. The controller 965 and the DSP 955 may include an interface, for example IEEE 1149.1, to provide in-circuit testing and programming capability. The controller 965 may also include an external oscillator such as a crystal oscillator.

The power conversion stages 990, 985, 970 may receive supply voltage, for example 24 Vdc, from the power supply bus 995. The supply voltage may be provided to the power bus 995 by an external transport or support module (not shown). The digital power conversation stage 990 may convert the supply voltage to appropriate voltage levels, for example +3.3 volts and +1.9 volts, for the digital circuitry, for example, the controller 965. The analog power conversion stage may convert the supply voltage to appropriate voltage levels, for example ±5 volts, for the analog circuitry, for example, the gain and filtering stages 930. The exciter power conversion stage may convert the supply voltage to appropriate voltage levels, for example +24 volts and +12 volts, for the exciter 920 drive. The power connections have not been shown in FIG. 9 for clarity. As may therefore be appreciated, FIG. 9 depicts one exemplary electronic circuit block diagram. One or more functional blocks may be combined into a single electronic component or may be divided into multiple components without diverting from the scope of the disclosure.

Although illustrative embodiments and methods have been shown and described, a wide range of modifications, changes, and substitutions is contemplated in the foregoing disclosure and in some instances some features of the embodiments or steps of the method may be employed without a corresponding use of other features or steps. Accordingly, it is appropriate that the claims be construed broadly and in a manner consistent with the scope of the embodiments disclosed herein.

What is claimed is:

1. A pipeline inspection device for a pipe comprising:
   an exciter coil capable of providing an alternating current magnetic field and producing eddy currents;
   a plurality of sensors capable of sensing a magnetic field produced by said eddy currents, said plurality of sensors engaged with a sensor shoe;
   said sensor shoe connected to a sensor support arm wherein said support arm is pivotably attached to a fixed hub and to a control arm;
   a driven hub pivotably attached to said control arm; and
   a lead screw, said lead screw engaged to and capable of positioning said driven hub along an axial axis of said pipeline inspection device;
   said sensors capable of being positioned at a first distance $D_1$ with respect to an inner pipe wall surface and capable of providing coupling to said magnetic field produced by said eddy currents;
   said sensor shoe capable of retracting to a second distance $D_2$, wherein $D_1 < D_2$.

2. The pipeline inspection device of claim 1 wherein said sensor shoe is positioned at an angle $\alpha$ with respect to an axial axis of said pipe, wherein $\alpha$ is about 0 degrees to about 90 degrees.

3. The pipeline inspection device of claim 1 further comprising a motor capable of turning said lead screw to adjust the position of said driven hub.

4. The pipeline inspection device of claim 1 wherein said control arm comprises a compliant strut.

5. The pipeline inspection device of claim 1 wherein said support arm is compliant.

6. The pipeline inspection device of claim 1 wherein said sensor shoe is biased against the pipe wall.

7. The pipeline inspection device of claim 1 wherein said sensor shoe comprises two or more articulating segments, each segment containing at least one sensor.

8. The pipeline inspection device of claim 1 wherein said exciter coil comprises a fixed diameter coil.

9. The pipeline inspection device of claim 1 wherein said exciter coil comprises a variable diameter coil.

10. The pipeline inspection system of claim 9 wherein said coil is capable of contracting and expanding by winding and unwinding.

11. The pipeline inspection system of claim 1 including a plurality of sensor shoes and a plurality of control arms.

12. A pipeline inspection device comprising:
   an exciter coil capable of providing an alternating current magnetic field and producing eddy currents;
   a plurality of sensors capable of sensing a magnetic field produced by said eddy currents, said plurality of sensors engaged with a sensor shoe;
   said sensors capable of being positioned at a first distance $D_1$ with respect to an inner pipe wall surface and capable of providing coupling to said magnetic field produced by said eddy currents;
   said sensor shoe capable of retracting to a second distance $D_2$, wherein $D_1 < D_2$;
   exciter drive electronic circuitry capable of providing an alternating current drive signal to said exciter coil;
   sensor position control electronic circuitry capable of detecting and controlling said sensor position; and
   sensor signal processing circuitry capable of receiving and processing a sensor signal representative of a sensed magnetic field;
   said sensor signal processing circuitry comprising a digital signal processor configured to receive said one sensor signal and a synchronization signal, to perform a lock-in amplifier function on said one sensor signal and to generate an in-phase component and a quadrature component of said one sensor signal with respect to said synchronization signal.

13. The pipeline inspection device of claim 12 wherein said exciter drive electronic circuitry further comprises a direct digital synthesizer configured to generate the alternating current exciter drive signal.

14. A method of inspecting a pipe comprising:
- providing an exciter coil capable of providing an alternating current magnetic field and producing eddy currents;
- providing one or a plurality of sensors capable of sensing a magnetic field produced by said eddy currents wherein said sensors are engaged with a sensor shoe;
- positioning said sensor shoe at a first distance $D_1$ with respect to an inner pipe wall surface to provide coupling to said magnetic field produced by said eddy currents;
- sensing said magnetic field produced by said eddy currents; and
- retracting said sensor shoe to a second distance $D_2$, wherein $D_1 < D_2$;
- wherein said positioning of said sensor shoe at said first or second distance comprises connecting said sensor shoe to a support arm wherein said support arm is pivotably attached to a fixed hub and to a control arm wherein said control arm is pivotably attached to a driven hub and positioning said driven hub along an axial axis of said pipeline inspection device using a lead screw engaged with said driven hub.

15. The method of claim 14 wherein said sensors are positioned at an angle $\alpha$ with respect to an axial axis of said pipe, wherein $\alpha$ is about 0 degrees to about 90 degrees.

* * * * *